(12) United States Patent
Rothschild

(10) Patent No.: US 9,563,600 B2
(45) Date of Patent: Feb. 7, 2017

(54) SYSTEM AND METHOD FOR MONITORING AND DISPENSING DOSES OF MEDICATION

(76) Inventor: Leigh M. Rothschild, Sunny Isles Beach, FL (US)

( * ) Notice: Subject to any disclaimer, the term of this patent is extended or adjusted under 35 U.S.C. 154(b) by 736 days.

(21) Appl. No.: 13/592,378

(22) Filed: Aug. 23, 2012

(65) Prior Publication Data

US 2014/0058561 A1 Feb. 27, 2014

(51) Int. Cl.
G06F 17/00 (2006.01)
A61J 1/03 (2006.01)
A61J 7/00 (2006.01)
A61J 7/04 (2006.01)

(52) U.S. Cl.
CPC ............... *G06F 17/00* (2013.01); *A61J 1/03* (2013.01); *A61J 7/0076* (2013.01); *A61J 7/0409* (2013.01); *A61J 2200/30* (2013.01)

(58) Field of Classification Search
CPC .......... A61J 1/03; A61J 7/0076; A61J 7/0409; A61J 2200/30
USPC ........................................................ 700/244
See application file for complete search history.

(56) References Cited

U.S. PATENT DOCUMENTS

| | | | |
|---|---|---|---|
| 4,460,106 A * | 7/1984 | Moulding, Jr. .... | B65D 83/0409 221/1 |
| 8,108,068 B1 * | 1/2012 | Boucher ............... | A61J 7/0084 700/236 |
| 8,195,330 B2 * | 6/2012 | Coe ............................... | 700/243 |
| 8,666,539 B2 * | 3/2014 | Ervin ........................ | A61J 1/03 700/236 |
| 8,670,865 B2 * | 3/2014 | Coe ............................... | 700/243 |
| 2004/0158350 A1 * | 8/2004 | Ostergaard et al. .......... | 700/231 |
| 2006/0071011 A1 * | 4/2006 | Varvarelis et al. ............... | 221/9 |
| 2007/0024465 A1 * | 2/2007 | Howell .................... | A61B 5/01 340/870.01 |
| 2007/0185615 A1 * | 8/2007 | Bossi ................... | G06F 19/3462 700/244 |
| 2008/0035661 A1 * | 2/2008 | Handfield et al. .............. | 221/13 |
| 2011/0133948 A1 * | 6/2011 | Ervin ............................ | 340/687 |
| 2012/0101630 A1 * | 4/2012 | Daya et al. .................... | 700/231 |
| 2013/0035785 A1 * | 2/2013 | MacVittie .......... | B65D 83/0409 700/231 |
| 2014/0055267 A1 * | 2/2014 | Rothschild ............ | A61J 7/0084 340/573.1 |
| 2014/0058561 A1 * | 2/2014 | Rothschild ................ | A61J 1/03 700/244 |

\* cited by examiner

*Primary Examiner* — Michael K Collins
(74) *Attorney, Agent, or Firm* — Eugenio J. Torres-Oyola; Victor Rodriguez-Reyes; Ferraiuoli LLC

(57) ABSTRACT

Devices, systems and methods for monitoring medication are provided. A medication monitoring device according to one implementation includes a container configured to store a plurality of medication pills and a gating device connected at an opening of the container. The gating device is configured to electronically monitor the release of at least one of the medication pills. A system and method for monitoring the administration of medication to a patient are also provided. The system, according to one embodiment, comprises the medication monitoring device and a medication management server in communication with the medication monitoring device via a communication network.

25 Claims, 2 Drawing Sheets

SYSTEM AND METHOD FOR MONITORING AND DISPENSING DOSES OF MEDICATION

TECHNICAL FIELD

The present disclosure generally relates to medication dispensing systems, and more particularly relates to monitoring doses of medication being dispensed.

BACKGROUND

Medication is prescribed for patients who may have various types of illnesses or medical conditions. Medication can have many different forms and can be administered to patients in a number of ways. For example, some medication may have a solid form, while other medication may be in the form of liquid, cream, vapor, etc. For solid medication (e.g., pills, tablets, capsules, etc.), a patient may use a pill organizer, also referred to as a pill box or pill container. Pill organizers are used to help patients maintain a proper schedule for taking one or more pills. Many pill organizers may have a total of seven separate compartments, where each compartment may have a square or rectangular shape and may represent a specific day of the week.

When a pill organizer is used and medication is correctly placed in the different compartments for a week, it can be easier for the patient to find out if a dosage has been taken for each day. If it is seen that the compartment is empty for a particular day, then the patient knows that he/she has already taken the medication. Otherwise, if medication is remaining in the compartment, then the patient knows that the medication has not yet been taken and can then take it as prescribed. Therefore, the pill organizer can help the patient reduce errors associated with the administration of the medication. Particularly, the pill organizer can reassure that the medication is taken at the correct times throughout the week without missing a day and without overmedicating. Although a pill organizer can be a useful tool for keeping a patient on a regular medication schedule, there may be times when additional monitoring is needed.

SUMMARY

The present disclosure describes devices, systems and methods for monitoring medication and monitoring the release of medication to a patient. A medication monitoring device, according to one embodiment, comprises a container configured to store a plurality of medication pills and a gating device connected at an opening of the container. The gating device is configured to electronically monitor the release of at least one of the medication pills.

A system and method for administering the release of medication to a patient are also disclosed herein. The system comprises a medication monitoring device and a medication management server. The medication monitoring device includes a container configured to store medication pills and a gating device configured to monitor the release of at least one of the medication pills. The medication management server is configured to be in communication with the medication monitoring device via a communication network.

In one aspect of the present disclosure, a method for monitoring the administration of medication to a patient includes storing medication pills in a container of a medication monitoring device; monitoring the release of at least one of the medication pills via a gating device of the medication monitoring device; and coupling a medication management server in communication with the medication monitoring device via a communication network.

In another aspect, the method further includes transmitting, by the medication management server, an indication to an electronic mobile device associated with a patient when it is time for the patient to receive at least one of the medication pills. The indication may be communicated to the electronic mobile device via a text message or an e-mail message.

BRIEF DESCRIPTION OF THE DRAWINGS

The features illustrated in the following figures are intended to emphasize the general principles of the present disclosure and are not necessarily drawn to scale. Consistent reference characters are used throughout the figures to designate corresponding features.

DETAILED DESCRIPTION

The present disclosure describes systems and methods for dispensing medication and also monitoring the doses of medication as they are being dispensed. Although pill organizers are useful in many situations, additional control and management of the dispensing of medication provides benefits to both the patients taking the medication and to doctors or other health care professionals who may need to monitor and oversee the actual administration of medication to their patients. According to the implementations of the present disclosure, systems and methods for monitoring and managing the administration of medication are described herein.

Figure 1:
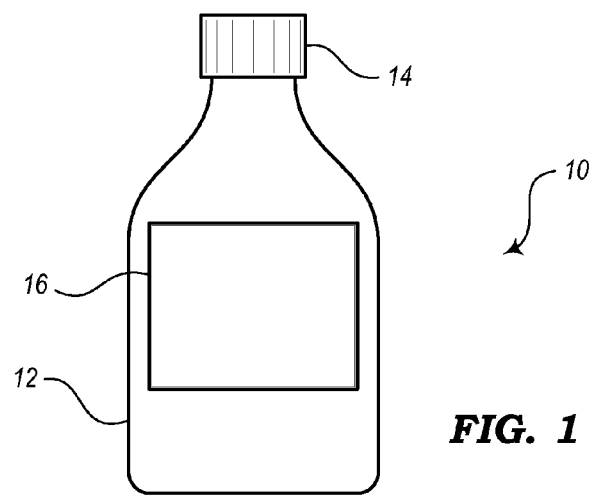
FIG. 1 is a diagram illustrating a front view of a medication monitoring device, according to one embodiment.

FIG. 1 is a diagram illustrating an embodiment of a medication monitoring device 10. The medication monitoring device 10 comprises a housing 12, a cap 14, and a user interface 16. As shown in FIG. 1, the housing 12 may have an outside surface that resembles an ordinary bottle or container for medication, although in other embodiments it may have any other suitable appearance. It should be noted that the housing 12 may have any shape or color and may comprise any suitable material. The housing 12 is configured to include at least a container for storing a plurality of pills. According to the present disclosure, the term "pill" may include any type of tablet or capsule, wherein the tablet or capsule is either completely solid or has at least a solid or mostly solid outer shell or surface, and wherein the tablet or capsule contains a predefined amount of medication. The pill may include any shape, size, color, or other features typical of such medication.

The cap 14 may include a lock device for locking the cap 14 in a closed position. The lock device may be able to prevent anyone except for an authorized party to unlock the cap 14. For example, the authorized party may include pharmacists, physicians, or other health care professional. In some embodiments, the lock device may be designed such that it may be locked and/or unlocked remotely by the authorized party. For example, a signal may be communicated to the medication monitoring device 10 from the remote authorized party via any suitable communication protocol (e.g., e-mail, Wi-Fi, Bluetooth, etc.), wherein the signal may cause the lock device of the cap 14 to lock or unlock as needed.

As shown in FIG. 1, the user interface 16 may be placed on a front, outside surface of the housing 12, or, according to other designs, may be placed on any accessible surface of the housing 12 or cap 14. The user interface 16 may be configured to allow a user to enter information regarding the type of pills to be stored in the housing 12, the dosage of medication, patient information, etc. In some embodiments, the user interface 16 may include a touch screen to allow input from the user as well as provide output information to the user. Some information may be provided upon demand, such as if the user presses a button or key on the touch screen. It should be understood that the user is not necessarily (but may be) the same person as the patient to whom the medication is prescribed, but instead may be a pharmacist, physician, nurse, or other health care professional.

According to various embodiments, the user interface 16 may be regarded as an optional element or it may be omitted. In other embodiments, the user interface 16 may further include or may be replaced with a label or electronic label. The electronic label (or user interface 16) may be configured to display warnings or notes, such as dosage warnings or other types of notifications. The electronic label (or user interface 16) may also provide notifications of times that the patient is supposed to take the pills. According to some implementations, the electronic label (or user interface 16) may include electronic paper, or e-paper, and conform to the shape of the housing 12.

Figure 2:
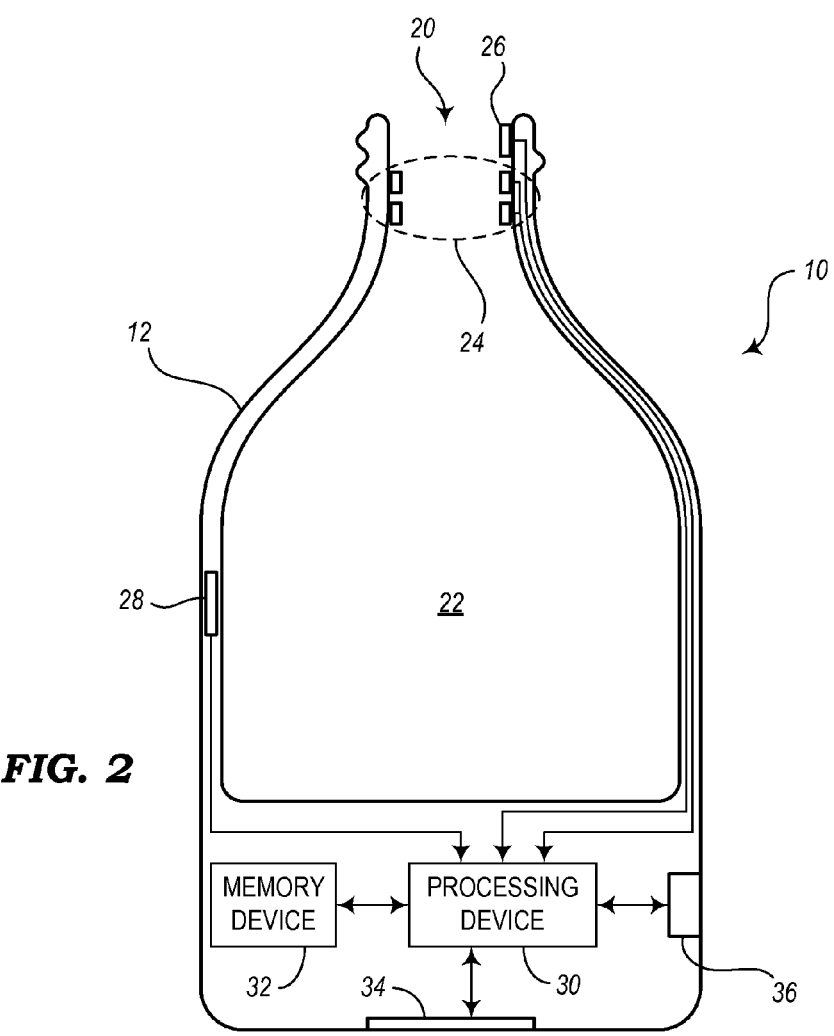
FIG. 2 is a diagram illustrating a cross-sectional view of the medication monitoring device of FIG. 1, according to one embodiment.

FIG. 2 is a cross-sectional view of the medication monitoring device 10 shown in FIG. 1 with the cap 14 removed. As illustrated in FIG. 2, the housing 12 of the medication monitoring device 10 includes an opening 20 and a container 22. The opening 20 leads into the container 22, which forms an interior portion of the housing 12. The container 22 may be configured to include a sufficient size to accommodate a plurality of pills (not shown). Also, the opening 20 includes a sufficient size to allow the pills to be inserted into and removed from the container 22.

In addition to the physical characteristics of the housing 12, the medication monitoring device 10 further includes electronic circuitry that is incorporated into the housing 12. Some of the electronic circuitry may be formed in a separate compartment from the container 22 to avoid contact between the pills and the electronic circuitry. Attached near the opening 20 are a gating device 24 and an imaging device 26. The medication monitoring device 10 further comprises a temperature sensor 28, which may be formed, for example, in a side wall of the housing 12. Electrical conductors from the gating device 24, imaging device 26, and the temperature sensor 28 may be incorporated within the walls of the housing and may provide communication between these components and additional electrical circuitry incorporated in another part of the housing 12, such as in a bottom portion of the housing 12, as shown. The additional electrical circuitry of the medication monitoring device 10 includes a processing device 30, a memory device 32, a reader device 34, and a communication device 36.

The gating device 24 may have electrical and/or electromechanical characteristics, depending on the particular embodiment. The gating device 24 may be configured to have a specific size and/or shape to allow the pills to be inserted into and removed from the container 22 at least one at a time with little resistance. In some embodiments, the gating device 24 may be configured such that only a single pill can be removed at a time. Also, the gating device 24 may include various physical properties allowing it to be adjusted so that its opening can be changed in size and/or shape to accommodate different sizes of pills. Therefore, the gating device 24 may be adjusted to allow pills having a particular size and/or shape to be inserted within or removed from the container 22. In some embodiments, the size and/or shape of the opening of the gating device 24 may be continually controlled to allow only a prescribed dosage of pills to be dispensed at regularly scheduled times, thereby preventing a patient from taking too much medication within a certain time period.

In addition, the gating device 24 includes one or more sensors configured to sense when a pill passes thereby. In this respect, the sensor(s) of the gating device 24 are able to monitor when a pill is being removed from the container 22 and when a pill is inserted into the container 22. The sensors of the gating device 24 may have any suitable size and shape. Also, the sensors may operate in a manner such that they make physical contact with the pills as they pass through the opening 20 or alternatively may operate using contactless sensing without making physical contact. The contact-type sensors of the gating device 24, for example, may include physical trip gates or turnstile-type gate. Contactless sensors may include laser sensors, light sensors, optical sensors, capacitance sensors, proximity sensors, or other types of contactless sensing mechanisms.

As illustrated, the gating device 24 may include two levels of sensors, where one level of sensors is positioned closer to the mouth of the opening 20. In this respect, the gating device may be able to sense the direction of movement of a pill passing through the opening 20. For example, if a top level of sensors (located nearest to the mouth of the opening 20) senses a pill passing through the opening 20 before a bottom level of sensors senses it, then it can be determined that the pill is being inserted into the container 22. On the other hand, if the bottom level senses the pill before the top level does, it can be determined that the pill is being removed from the container 22. According to other embodiments, the gating device 24 may only require one level of sensors (such as for contact-type sensors) or may include more than two levels of sensors, depending on the particular type and operation of the sensors used.

The imaging device 26 of the medication monitoring device 10 may be optional or may be omitted in various embodiments. The imaging device 26 is configured to capture an image of a marking on a pill as it passes through the opening 20. For example, the pill may have markings, etchings, or other visual indicia that identify certain aspects of the pill, such as the type and dosage of the medication. The imaging device 26 may include one or more charge-coupled devices (CCDs) or other suitable visual sensing devices.

The temperature sensor 28 may also be optional and may be omitted if not used in some embodiments. The temperature sensor 28 is configured to sense the temperature of the housing 12. Since some types of medication may be negatively affected by extreme temperatures, the temperature sensor 28 can help to determine when there is an increased chance that the effectiveness of the medication may deteriorate quicker than usual.

The gating device 24, imaging device 26, and temperature sensor 28 (or any combination of these elements used in the various implementations) are connected to the processing device 30. The processing device 30 is configured to control the overall operations of the medication monitoring device 10. When signals are received by the various sensors, the processing device 30 is configured to process the signals to determine different conditions, such as whether a pill has been removed from the container 22, how many pills are left in the container 22, an identification element of a pill passing through the opening 20, and other functions. Furthermore, the processing device 30 may be configured to determine from a sensed image from the imaging device 26 whether or not the sensed image matches the type of medication that is stored within the container 22. The processing device 30 may also be configured to generate reminders and warnings to be sent to the user interface 16 or to a remote location via the communication device 36.

The memory device 32 is configured to store records of the types of medication being held within the container 22, the dates and times that the pills were placed into the container 22, the dates and times that the pills were removed from the container 22, etc. Also, the memory device 32 may store information regarding the medication, such as type, dosage, expiration information, images of various types of pills, types of markings applied to the medication, etc. The memory device 32 may also store information about the patient, such as name, age, medical conditions, insurance carrier, patient's doctor's name, etc.

The reader device 34 shown in FIG. 2 may include any suitable type of scanner or sensor for sensing a visual image or electronic signal. For example, the reader device 34 may include a barcode reader for reading barcodes. In some embodiments, drug information may be coded into a barcode that is readable by the reader device 34 to obtain the drug information by simply scanning the barcode. The barcode may include coded information regarding prescriptions, dosages, expiration dates, patients, medication type, etc. According to some implementations, the reader device 34 may include a radio frequency identification (RFID) sensor for sensing an RFID signal, which may be associated with medication information. According to other implementations, the reader device 34 may include one or more charge-coupled devices (CCDs) or other suitable visual sensing devices for reading information from a prescription which is then transmitted to the processing device 30 for optical character recognition (OCR).

The communication device 36 may be configured to communicate with a remote device by a wired or a wireless channel. For example, wireless communication may include Wi-Fi, radio frequency identification (RFID), Bluetooth, or other wireless protocol. Wired communication may include a connector adapted to universal serial bus (USB) protocols, FireWire protocols, or other suitable types of electrical connector protocols. The communication device 36 therefore allows the medication monitoring device 10 to communicate with doctors, pharmacists, drug manufacturers, and others, as described in more detail below with respect to the description of FIG. 3.

Alerts from the medication monitoring device 10 may be provided by the communication device 36 via a website, text message, e-mail, a push alert, or other technique. The communication device 36 may also communicate with a user's (patient's) local mobile device, such as a cellular phone or smart phone, or may communicate with the user's personal computer or laptop computer. In some embodiments, the communication device 36 may communicate or download information stored in the memory device 32 to a remote device, such as a physician's or medical professional's computer.

According to some implementations of the present disclosure, the medication monitoring device 10 may simply comprise a container 22, configured to store a plurality of medication pills, and a gating device 24 connected at an opening 20 of the container 22. The gating device 24 may be configured to electronically monitor the release of at least one of the medication pills. The medication monitoring device 10 may further comprise a processing device 30 configured to receive signals from the gating device 24 indicating the release of the at least one medication pill. The medication monitoring device may further comprise an imaging device 26 configured to obtain an image of the at least one medication pill being released and to identify the type of the at least one medication pill based on a marking on the at least one medication pill. The processing device 30 may further be configured to determine whether or not the identified type of the at least one medication pill matches a correct medication pill intended to be stored in the container 22.

The medication monitoring device may further comprise a memory device 32 configured to store information regarding the release of the at least one medication pill. The memory device may be configured to store date and time information regarding the release of the at least one medication pill. The memory device may further be configured to store medication type information, medication dosage information, and patient information. In some embodiments, the medication monitoring device 10 may be configured such that the gating device 24 comprises an opening having an adjustable size to accommodate the release of the at least one medication pill.

The medication monitoring device 10 may further comprise a communication device 36 configured to communicate an alert to a patient indicating a time for administering the at least one medication pill. The communication device 36 may further be configured to communicate with a remote electronic device, which may include wirelessly communicating with the remote electronic device. In some embodiments, the communication device 36 may comprise a communication port and be configured to communicate with the remote electronic device via the communication port and a wired or wireless connection.

According to some embodiments, the medication monitoring device 10 may further comprise a reader device 34 configured to read symbology related to prescription information. For instance, the reader device 34 may be a bar code scanner and the symbology be may a bar code. The prescription information, for example, may include medication type information, dosage information, patient information, and medication expiration information.

The medication monitoring device 10 mentioned above may also comprise a lock device configured to restrict access to the medication pills to only an authorized party. In some embodiments, the lock device may be configured to be locked and unlocked remotely.

The medication monitoring device 10 may further comprise a user interface 16 attached to an exterior portion of the container 22. The user interface 16 may be configured to enable a user to enter medication identification information, dosage information, and patient information. Furthermore, the user interface may also comprise a touch screen device. In additional and/or alternative embodiments, the medication monitoring device may be configured such that it further comprises an electronic label configured to provide notification of medication schedules and dosages.

Figure 3:
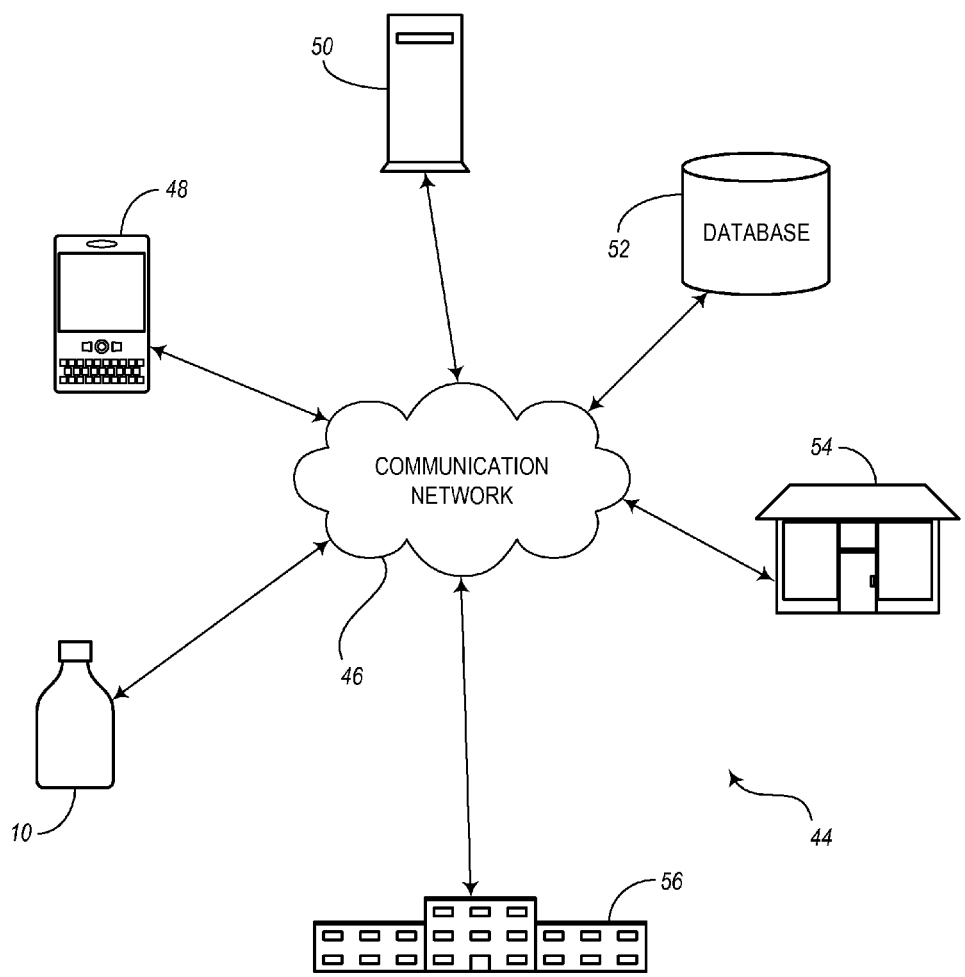
FIG. 3 is a block diagram illustrating a system for monitoring the administration of a medication to a patient, according to one embodiment.

FIG. 3 is a block diagram illustrating a system 44 for communicating medication information among various electronic components. The system 44, as shown, comprises a communication network 46, which may include a data network, such as the Internet, wide area network, local area network (LAN), and/or any suitable types of data networks.

The communication network 46 may additionally include a telephone network, cellular phone network, or other suitable types of wired or wireless data, text, and/or voice networks.

The system 44 also includes the medication monitoring device 10, which is described in detail with respect to FIGS. 1 and 2, in communication with the communication network 46. The medication monitoring device 10 may be connected to the communication network 46 using wireless and/or wired communication components. The communication network 46 also communicates wirelessly or by wired connection with one or more mobile devices 48 (being used by a patient, physician, health care professional, or other person), a medication management server 50, a medication interaction database 52, a computer associated with a pharmacy 54, and a computer associated with a drug manufacturer 56.

In some embodiments, the medication monitoring device 10 may communicate with any or all of the mobile devices 48, server 50, database 52, pharmacy 54, and drug manufacturer 56 via the communication network 46. The medication monitoring device 10 may also be configured to communicate with a local computer (not shown), e.g., a computer of a user of the medication monitoring device, which in turn may communicate information on behalf of the medication monitoring device 10 to the other nodes via the communication network 46.

The medication management server 50 and medication interaction database 52, according to various implementations, may be incorporated together to operate as a single entity over the communication network 46. The medication management server 50 may be configured to receive information from various sources within the system 44 to control various aspects of the system 44. In some embodiments, the medication management server 50 may comprise a website server for offering a website to patients, physicians, pharmacists, and others. The medication management server 50 may store information regarding medication types, dosages, expiration dates, patients, medication schedules, related information, medication rebates or offers, authorized parties for administering medication to the patients, etc. The database 52 may store website information, which the server 50 may provide to various users. In this respect, website information, texts, e-mail information, and push alerts may be provided to the users as needed.

The server 50 may be accessible by physicians, monitoring services, health care providers, patients, legal guardians or representatives for the patients, or others. The server 50 may provide signals regarding overdose warnings, drug expiration warnings, temperature warnings, or other types of warnings. Also, the server 50 may store into the database 52 information regarding medication history for multiple patients, medication remaining for each patient, verification of drug authenticity, and other information. In some embodiments, the server 50 may send e-mail or text messages to a patient via the patient's mobile device 48 to remind the patient to take his/her medication. Also, messages to take medication may be accompanied with other information, such as dosage amounts to be taken, whether or not the medication is to be taken with food, or other suitable messages. In some embodiments, the server 50 may send messages, e.g., reminders, recall information, etc., to the medication monitoring device 10 where the messages are to be displayed or provided to the user via the user interface 16.

According to some implementations of the present disclosure, the system 44 may be configured for monitoring the administration of medication to a patient. The system 44, according to one implementation, may simply comprise a medication monitoring device 10 in communication with a medication management server 50 via a communication network 46, wherein the medication monitoring device 10 comprises a container 22 configured to store medication pills and a gating device 24 configured to monitor the release of at least one of the medication pills.

The system 44, according to additional embodiments, may further comprise an electronic mobile device 48 associated with a patient, wherein the medication management server 50 is configured to provide an indication to the patient via the electronic mobile device 48 when it is time for the patient to receive at least one of the medication pills. The system 44 may further comprise a medication interaction database 52 in communication with the communication network 46. The medication interaction database 52 may be configured to store information related to an overdose warning, medication expiration, medication administration history, amount of remaining medication, and a verification of authenticity. Information in the medication interaction database 52 may be accessible by at least one person including a physician, health care provider, patient, or legal representative of the patient. The information in the medication interaction database 52 may be communicated to the at least one person via a website, text message, e-mail message, or push alert.

In some embodiments, the system 44 may further comprise a pharmacy computer 54 in communication with the communication network 46, wherein the medication management server 50 is configured to submit a request for an automatic medication refill order to the pharmacy computer 54, based on the amount of medication left in the medication monitoring device 10. In one embodiment, the medication monitoring device 10 transmits the amount of medication dispensed and the medication management server 50 determines how much medication should be remaining in the medication monitoring device 10. Based on a predetermined threshold, e.g., a low limit quantity, the medication management server 50 submits a request for an automatic medication refill order to the pharmacy computer 54. When the refill order is complete, the pharmacy computer 54 confirms the order is filled by transmitting a message to the medication management server 50, which subsequently informs a user of the medication monitoring device 10 via, for example, a text message, e-mail, etc., to the electronic mobile device 48 or transmits this information directly to the medication monitoring device 10 for display on the user interface 16.

The system may also comprise a drug manufacturer computer 56 in communication with the communication network 46, wherein the drug manufacturer computer 56 may be configured to provide drug recall information and drug warnings and medication offers and rebates to the medication management server 50 as needed. This information may be communicated to the at least one person via a website, text message, e-mail message, or push alert. For example, a rebate offer may be pushed to the user's mobile device 48 or directly to the medication monitoring device 10 where the information may be displayed via the user interface 16.

In one embodiment, the medication monitoring device 10 may be configured to transmit the image of the at least one medication pill to the medication management server 50 for verification of authenticity. In another embodiment, the medication monitoring device 10 may be configured to compare the image of the at least one medication pill to at least one image stored in the memory device 32 for verification of authenticity.

It is to be appreciated that any information provided to the medication management server 50 may be provided to a user of the medication monitoring device 10 via, for example, a text message, e-mail, etc., to an electronic mobile device 48 of the user or provided directly to the medication monitoring device 10 for display on the user interface 16.

The various implementations described herein are not intended to limit the present disclosure, but may include additional features and advantages not necessarily expressed herein. The additional features and advantages may be apparent to one of ordinary skill in the art upon examination of the detailed description and accompanying drawings, according to spirit and scope of the present disclosure. It is intended that all such additional features and advantages be included within the present disclosure and protected by the accompanying claims.

I claim:

1. A system for monitoring the administration of medication to a patient, the system comprising:
    a medication monitoring device having a container configured to store medication pills and a gating device that includes two levels of one or more sensors wherein a top level of one or more sensors is positioned substantially closer to an opening of the medication monitoring device and a bottom level of one or more sensors is positioned substantially closer to a bottom surface of the medication monitoring device such that:
        the gating device determining a medication pill is inserted into the medication monitoring device when the top level of one or more sensors senses a medication pill prior to the bottom level of one or more sensors sensing the medication pill; and
        the gating device determining a medication pill is released from the medication monitoring device when the bottom level of one or more sensors senses the medication pill prior to the top level of one or more sensors sensing the medication pill;
    wherein the medication monitoring device further comprises a user interface attached to an exterior portion of the container, the user interface includes a touch screen device and the user interface receives medication identification information, dosage information, and patient information;
    wherein the medication monitoring device further comprises an imaging device configured to obtain an image of the at least one medication pill being released and to identify the type of the at least one medication pill based on a marking on the at least one medication pill;
    wherein the medication monitoring device further comprises a temperature sensor that records a temperature within the medication monitoring device;
    wherein the medication monitoring device further comprises a processing device that receives the medication identification information, dosage information, patient information, an image of at least medication pill, and the temperature;
    a medication management server in communication with the medication monitoring device via a communication network;
    wherein the processing device of the medication monitoring device sends a message to the medication management server based on the medication identification information, dosage information, patient information, an image of at least medication pill, and the temperature.

2. The system of claim 1, further comprising an electronic mobile device associated with a patient, wherein the medication management server is configured to provide an indication to the patient via the electronic mobile device when it is time for the patient to receive at least one of the medication pills.

3. The system of claim 2, wherein the indication is communicated to the electronic mobile device via a text message.

4. The system of claim 1, wherein the indication is communicated to the electronic mobile device via an e-mail message.

5. The system of claim 1, further comprising a medication interaction database in communication with the communication network.

6. The system of claim 5, wherein the medication interaction database is configured to store information related to an overdose warning, medication expiration, medication administration history, amount of remaining medication, and a verification of authenticity.

7. The system of claim 5, wherein information in the medication interaction database is accessible by at least one person including a physician, health care provider, patient, or legal representative of the patient.

8. The system of claim 7, wherein the information in the medication interaction database is communicated to the at least one person via a website, text message, e-mail message, or push alert.

9. The system of claim 1, further comprising a computer associated with a pharmacy, the computer configured in communication with the communication network, wherein the medication management server is configured to submit a request for an automatic medication refill order to the computer.

10. The system of claim 1, further comprising a computer associated with a drug manufacturer, the computer configured in communication with the communication network, wherein the computer associated with the drug manufacturer is configured to provide drug recall information, drug warnings, drug offers and drug rebates to the medication management server as needed.

11. The system of claim 1, wherein the medication monitoring device further comprises a lock device configured to restrict access to the medication pills to an authorized party.

12. The system of claim 11, wherein the lock device is configured to be locked and unlocked remotely via the medication management server.

13. The system of claim 1, wherein the medication management server is configured to provide an indication to the patient via the user interface when it is time for the patient to receive at least one of the medication pills.

14. The system of claim 1, wherein the medication monitoring device is configured to transmit the image of the at least one medication pill to the medication management server for verification of authenticity.

15. A method for monitoring the administration of medication to a patient comprising:
    monitoring at least one of the medication pills via a gating device of the medication monitoring device; wherein the gating device includes two levels of one or more sensors wherein a top level of one or more sensors is positioned substantially closer to an opening of the medication monitoring device and a bottom level of one or more sensors is positioned substantially closer to a bottom surface of the medication monitoring device such that:
        the gating device determining a medication pill is inserted into the medication monitoring device when the top level of one or more sensors senses a medication pill prior to the bottom level of one or more sensors sensing the medication pill; and the gating device determining a medication pill is released from the medication monitoring device when the bottom level of one or more sensors senses the medication pill prior to the top level of one or more sensors sensing the medication pill; and receiving, by a user interface having a touchscreen, medication identification information, dosage information, and patient information;

obtaining, by an imaging device, an image of the at least one medication pill being released and to identify the type of the at least one medication pill based on a marking on the at least one medication pill;

recording, by a temperature sensor, a temperature within the medication monitoring device;

receiving, by a processing device, the medication identification information, dosage information, patient information, an image of at least medication pill, and the temperature;

coupling a medication management server in communication with the medication monitoring device via a communication network;

sending, by the processing device, a message to the medication management server based on the medication identification information, dosage information, patient information, an image of at least medication pill, and the temperature.

16. The method of claim 15, further comprising transmitting, by the medication management server, an indication to an electronic mobile device one of the medication pills.

17. The method of claim 16, wherein the indication is communicated to the electronic mobile device via a text message.

18. The method of claim 16, wherein the indication is communicated to the electronic mobile device via an e-mail message.

19. The method of claim 15, further comprising coupling a medication interaction database in communication with the communication network.

20. The method of claim 19, wherein the medication interaction database is configured to store information related to an overdose warning, medication expiration, medication administration history, amount of remaining medication, and a verification of authenticity.

21. The method of claim 19, wherein information in the medication interaction database is accessible by at least one person including a physician, health care provider, patient, or legal representative of the patient.

22. The method of claim 21, wherein the information in the medication interaction database is communicated to the at least one person via a website, text message, e-mail message, or push alert.

23. The method of claim 15, further comprising submitting, by the medication management server, a request for an automatic medication refill order to a computer associated with a pharmacy, the computer configured in communication with the communication network.

24. The method of claim 15, further comprising:

providing a computer associated with a drug manufacturer, the computer configured in communication with the communication network; and transmitting, by the computer associated with the drug manufacturer, drug recall information, drug warnings, drug offers and drug rebates to the medication management server as needed.

25. The method of claim 15, wherein the medication monitoring device further comprises a lock device configured to restrict access to the medication pills to an authorized party, further comprising locking and unlocking the lock device remotely via the medication management server.

* * * * *